US007902426B1

(12) United States Patent
Hiei et al.

(10) Patent No.: US 7,902,426 B1
(45) Date of Patent: Mar. 8, 2011

(54) METHOD OF IMPROVING GENE TRANSFER EFFICIENCY INTO PLANT CELLS UTILIZING HEAT AND CENTRIFUGATION

(75) Inventors: Yukoh Hiei, Iwata-gun (JP); Keisuke Kasaoka, Oyama (JP); Yuji Ishida, Iwata-gun (JP)

(73) Assignee: Japan Tobacco Inc., Tokyo (JP)

( * ) Notice: Subject to any disclaimer, the term of this patent is extended or adjusted under 35 U.S.C. 154(b) by 633 days.

(21) Appl. No.: 10/089,695

(22) PCT Filed: Aug. 3, 2000

(86) PCT No.: PCT/JP00/05214
§ 371 (c)(1),
(2), (4) Date: May 21, 2002

(87) PCT Pub. No.: WO02/12521
PCT Pub. Date: Feb. 14, 2002

(51) Int. Cl.
*C12N 15/82* (2006.01)
(52) U.S. Cl. .......................... 800/294; 800/278; 435/468
(58) Field of Classification Search .................. 800/294, 800/306, 320.1, 320.2; 435/412, 424
See application file for complete search history.

(56) References Cited

U.S. PATENT DOCUMENTS

| | | | |
|---|---|---|---|
| 4,693,976 A | 9/1987 | Schilperoort et al. | |
| 4,940,838 A | 7/1990 | Schilperoort et al. | |
| 5,591,616 A * | 1/1997 | Hiei et al. ................. | 435/469 |
| 5,731,179 A | 3/1998 | Komari et al. | |
| 6,162,965 A | 12/2000 | Hansen | |
| 6,215,051 B1 | 4/2001 | Yu et al. | |
| 6,329,571 B1 | 12/2001 | Hiei | |

FOREIGN PATENT DOCUMENTS

| | | | |
|---|---|---|---|
| EP | 0159418 B1 | | 10/1985 |
| EP | 0116718 B1 | | 5/1990 |
| EP | 0504869 A2 | | 9/1992 |
| EP | 0672752 A1 | | 9/1995 |
| EP | 0927765 A1 | | 7/1999 |
| EP | 1136560 A1 | | 9/2001 |
| JP | 2000 342255 A | | 12/2000 |
| JP | 2001 29075 A | | 2/2001 |
| WO | WO-98-54961 | * | 12/1998 |
| WO | WO 98/54961 A2 | | 12/1998 |

OTHER PUBLICATIONS

Forreiter, et. al. (Stable transformation of an *Arabidopsis thaliana* cell suspension culture with firefly luciferase providing a cellular system for analysis of chaperone activity in vivo, Plant Cell, vol. 9, pp. 2171-2181, 1997).*
Cooper (The Tools of Biochemsitry, T. G. Cooper, John Wiley, New York, 1977, pp. 309, 1st full and p. 311 1st full ).*
Frame et. al. , 2006—Exhibit A—amendment dated Jan. 30, 2007.*
Zhao et al, 2006—Exhibit B—amendment dated Jan. 30, 2007.*
Shillito et al., 1994—Exhibit C—amendment dated Jan. 30, 2007.*
Indra et. al., 1991—Exhibit D—amendment dated Jan. 30, 2007.*
See Online Medical Dictionary print-out, Apr. 15, 2007, (//cancerweb.Incl. ac.uk/cgi-binary/omd).*
See Eppendorf Centrifuge 5418 print out from Eppendorf.com website, Jan. 19, 2007, p. 5 and p. 18.*
Wu et al. Heat stress responses in cultured plant cells. (1983) Plant Physiology; vol. 72; pp. 817-820.*
Lyznik et al. Heat-inducible expression of FLP gene in maize cells. (1995) The Plant Journal; vol. 8; pp. 177-186.*
Forreiter et al., The Plant Cell, vol. 9, 2171-2181, Dec. 1997.
Komari et al., "Methods of Genetic Transformation: *Agrobacterium tumefaciens*" Vasil (ed.) Molecular Improvement of Cereal Crops, 43-82, 1999, Kluwer Academic Publishers, Great Britain.
Hood et al., *Transgenic Research 2*, pp. 208-218 (1993).
Watson et al., *Journal of Bacteriology*, vol. 123, No. 1, pp. 255-264 (Jul. 1975).
Jefferson, *Plant Molecular Biology Reporter*, vol. 5, No. 4, pp. 387-405 (1987).
Toriyama et al., *Plant Science*, vol. 41, pp. 179-183 (1985).
Saito et al., *Theor Appl Genet*, vol. 83, pp. 679-683 (1992).
Ohta et al., *Plant Cell Physiol.*, vol. 31, No. 6, pp. 805-813 (1990).
Li et al., *Nature Biotechnology*, vol. 14, pp. 736-740 (Jun. 1996).
Komari et al., *The Plant Journal*, vol. 10, No. 1, pp. 165-174 (1996).
Komari et al., *Journal of Bacteriology*, vol. 166, No. 1, pp. 88-94 (Apr. 1986).
Komari, *Plant Cell Reports*, vol. 9, pp. 303-306 (1990).
Jin et al., *Journal of Bacteriology*, vol. 169, No. 10, pp. 4417-4425 (Oct. 1987).
Hood et al., *Bio/Technology*, vol. 2, pp. 702-709 (1984).
Ishida et al., *Nature Biotechnology*, vol. 14, pp. 745-750 (Jun. 1996).
Zambryski et al, *Ti plasmid vector for the introduction of DNA into plant cells without alteration of their normal regeneration capacity*, EHBO, pp. 2143-2150 (1983).
Hoekema et al., *Nature*, vol. 303, pp. 179-180 (May 1983).
Hood et al., *Journal of Bacteriology*, vol. 168, No. 3, pp. 1291-1301 (Dec. 1986).
Escudero et al., *Molecular Biology Protocols*, 106, pp. 599-602 (1994).
Xiao et al., *Plant Cell Reports*, vol. 16, pp. 874-878 (1997). Chilton et al., *Proc. Nat. Acad. Sci. USA*, vol. 71, No. 9, pp. 3672-3676 (Sep. 1974).
Chih-ching, *Plant Tissue Culture*, pp. 43-50 (Aug. 1978).
Ditta et al., *Proc. Natl. Acad. Sci., USA*, vol. 77, No. 12, pp. 7347-7351 (Dec. 1980).
Fraley et al., *Bio/Technology*, vol. 3, pp. 629-635 (Jul. 1985).
Fraley et al., *Proc. Natl. Acad. Sci. USA*, vol. 80, pp. 4803-4807 (Aug. 1983).
Hiei et al., *The Plant Journal*, vol. 6, No. 2 pp. 271-282 (1994).
Hartman et al., *Bio/Technology*, vol. 12, pp. 919-923 (Sep. 1994).
Bidney et al., *Plant Molecular Biology*, vol. 18, pp. 301-313 (1992).
Bevan, *Nucleic Acids Research*, vol. 12, No. 22, pp. 8711-8721 (1984).

(Continued)

*Primary Examiner* — Cathy Kingdon Worley
(74) *Attorney, Agent, or Firm* — Birch, Stewart, Kolasch & Birch, LLP

(57) ABSTRACT

A method for gene transfer by which higher efficiency for gene transfer than that by the conventional *Agrobacterium* method may be attained simply and without injuring the tissue is disclosed. According to the method of the present invention, the efficiency of gene transfer into plant cells by a bacterium belonging to genus *Agrobacterium* is promoted by accompanying heat treatment and centrifugation treatment of the plant cells or plant tissue.

10 Claims, 4 Drawing Sheets

OTHER PUBLICATIONS

Gelvin et al., *Plant Molecular Biology Manual*, Kluwar Academic Publishers, (1988).
Aldemita et al., *Planta*, vol. 199, pp. 612-617 (1996).
Visser, *Plant Tissue Culture Manual*, B5:1-9 (1991).
McCormick, *Plant Tissue Culture Manual*, B6:1-9 (1991).
Lindsey et al., *Plant Tissue Culture Manual*, B7:1-13 (1991).
Rogers et al., *Methods for Plant Molecular Biology*, pp. 423-437 (1998).
Zhong et al., *Plant Cell Reports*, vol. 13, pp. 1-6 (1993).
Hood et al., *Plant Physiol.*, vol. 83, pp. 529-534 (1987).
Horsch et al., *Science*, vol. 227, pp. 1229-1231 (Mar. 1985).
Komari, *Theor Appl. Genet*, vol. 80, pp. 167-171 (1990).
Potrykus et al., *Theor. Appl. Genet.*, vol. 54, pp. 209-214 (1979).
Komari, *Plant Science*, vol. 60, pp. 223-229 (1989).
Komari et al., *Molecular Improvement of Cereal Crops*, pp. 43-82 (1999).
Murashige et al., *Physiologia Plantarum*, vol. 15, pp. 473-497 (1962).
Asano et al., *Plant Cell Reports*, vol. 17, pp. 963-967 (1998).
Asano et al., *Plant Cell Reports*, vol. 13, pp. 243-246 (1994).
Trick et al., *Transgenic Research*, vol. 6, pp. 329-336 (1997).

* cited by examiner

METHOD OF IMPROVING GENE TRANSFER EFFICIENCY INTO PLANT CELLS UTILIZING HEAT AND CENTRIFUGATION

TECHNICAL FIELD

The present invention relates to a method for promoting efficiency of gene transfer into plant cells.

BACKGROUND ART

The method for transformation using *Agrobacterium* has a number of excellent features including, in general, the high efficiency, the small number of copies of the transferred gene, the feature that the gene may be transferred without fragmenting a specific region called T-DNA, and the feature that the frequency of mutation occurred during cultivation is low because transformants may be obtained by cultivation for a short period of time. Therefore, the method is widely used as the most useful method for transforming various plants.

Although the *Agrobacterium* method is an extremely excellent method for transforming plants, whether the transformation is successful or not and the transformation efficiency largely varies depending on the plant species, genotype and the plant tissue used (Potrykus et al. 1998 (Reference (36))). That is, there are species with which the transformation has not been successful, and species with which the transformation may be attained only with limited varieties. Further, there are species with which the tissue to be used is limited so that a large amount of materials cannot be treated. To prepare a practical variety by genetic recombination (genetic engineering), it is necessary to prepare a large number of transformed plants and to select the line having the desired character therefrom. However, at present, the type of plants with which a large number of transformed plants may be prepared for this purpose is limited. Thus, to develop an improved method by which this problem may be overcome is strongly demanded.

Although the method for transformation via *Agrobacterium* differs in the starting material, composition of the culture medium and the like, it is almost common to the *Agrobacterium* method that the method comprises making a tissue which is a starting material contact a suspension of *Agrobacterium*, selecting transformed cells after co-culturing, and growing transformed plants. The *Agrobacterium* is infected without performing a special treatment except for sterilization treatment which is carried out as required (Rogers et al. 1988 (Reference (37)), Visser 1991 (Reference (41)), McCormick 1991 (Reference (31)), Lindsey et al. 1991 (Reference (30))). Thus, studies for improving transformation system has been carried out mainly on the *Agrobacterium* strain, constitution of the vector, composition of medium, types of selection marker gene and promoter, the type of the tissue used as the material, and the like.

On the other hand, studies for changing the plant tissue before infection of *Agrobacterium* to a physiological state in which the genes are likely to be transferred have been scarcely made. If the physiological state of the tissue can be changed to such a physiological state by a simple treatment, the method is very useful, and it is expected that, in addition to the promotion of the transformation efficiency, transformation may be attained for the species or genotypes with which transformation has been hitherto difficult, that is a prominent effect. Known studies about pretreatment of plant tissue include particle gun treatment (Bidney et al., 1992 (Reference (6))) and ultrasonication treatment (Trick H. N. et al., 1997 (Reference (40))). Both of these methods aim at promoting invasion of bacteria into the plant tissue by physically injuring the tissue, so as to increase the number of plant cells infected. However, these methods are nothing more than developments of the leaf disk method (Horsch et al., 1985 (Reference (19))) and not treatments based on novel concepts. The degree of effectiveness and universality of the methods have not been clarified, and they are not used as general methods.

DISCLOSURE OF THE INVENTION

Accordingly, an object of the present invention is to provide a method for promoting efficiency of gene transfer into plant cells, by which gene transfer can be attained simply with a higher efficiency than the conventional gene transfer by *Agrobacterium* method, without injuring the tissue.

The present inventors intensively studied to discover that in the gene transfer method using *Agrobacterium*, the gene transfer efficiency may be significantly promoted by heating and centrifuging the plant cells or plant tissue subjected to the gene transfer, thereby completing the present invention.

That is, the present invention provides a method for promoting efficiency of gene transfer into plant cells by a bacterium belonging to genus *Agrobacterium*, comprising heating and centrifuging said plant cells or plant tissue.

By the present invention, a method for promoting efficiency of gene transfer into plant cells, by which gene transfer can be attained simply with a higher efficiency than the conventional gene transfer by *Agrobacterium* method, without injuring the tissue, has been provided. The method of the present invention may be applied to both monocotyledons and dicotyledons. Further, the plants such as creeping bent grass which could not be hitherto transformed by *Agrobacterium* method can be transformed by the method of the present invention.

Figure 1:
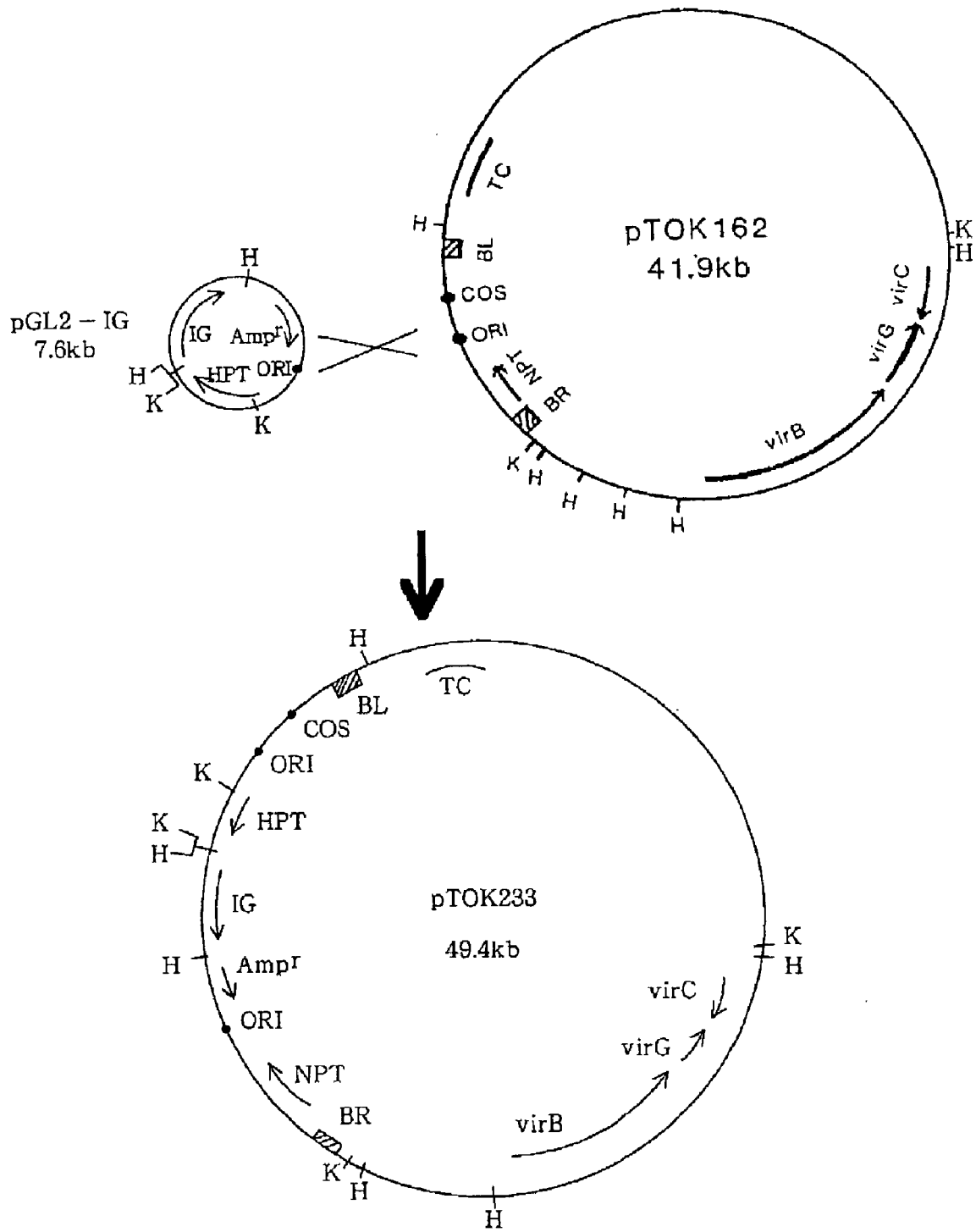
FIG. 1 is a drawing for showing a method for constructing pTOK233 which is an example of super-binary vectors, that may preferably be employed in the present invention.

In the above drawings, the following reference symbols denote the following meanings.

BL: left border sequence of T-DNA of bacteria belonging to genus *Agrobacterium*
BR: right border sequence of T-DNA of bacteria belonging to genus *Agrobacterium*
TC: tetracycline resistance gene
SP: spectinomycin resistance gene
IG: intron GUS gene
HPT: hygromycin resistance gene
NPT: kanamycin-resistance gene
K: restriction enzyme Kpn I site
H: restriction enzyme Hind III site
Amp': ampicillin resistance gene
BAR: bar gene COS, cos: COS site of λ phage ORI, ori: replication origin of ColE1

P35S: CaMV 35S promoter

Tnos: terminator of nopaline synthetase gene virB: the virB gene in the virulence region of Ti plasmid pTiBo542 contained in *Agrobacterium tumefaciens* A281 virC: the virC gene in the virulence region of Ti plasmid pTiBo542 contained in *Agrobacterium tumefaciens* A281 virG: the virG gene in the virulence region of Ti plasmid pTiBo542 contained in *Agrobacterium tumefaciens* A281

Vir: entire vir region of Ti plasmid of bacteria belonging to genus *Agrobacterium*

S Vir: entire vir region of Ti plasmid pTiBo542 of super virulent bacteria belonging to genus *Agrobacterium* s vir*: fragment containing a part of vir region of Ti plasmid pTiBo542

BEST MODE FOR CARRYING OUT THE INVENTION

The method of the present invention for promoting efficiency of gene transfer into plant cells by a bacterium belonging to genus *Agrobacterium*, comprises heating and centrifuging the plant cells or plant tissue. The plant cells or plant tissue may be contacted with the bacterium belonging to genus *Agrobacterium* under normal gravity after heating and centrifuging the plant cells or tissue, or the plant cells or tissue may be contacted with the bacterium belonging to genus *Agrobacterium* while heating and/or centrifuging the plant cells or tissue. In cases where the heat treatment and centrifugation treatment are carried out before making the plant cells or tissue contact the bacterium belonging to the genus *Agrobacterium*, these treatments may be carried out simultaneously, or one of these treatments may be carried out before the other treatment.

The conditions of the heat treatment may appropriately be selected depending on the type of the plant used and the like, and may usually be carried out at a temperature of 30° C. to 60° C., preferably 33° C. to 55° C., more preferably 37° C. to 52° C. The time of the heat treatment may appropriately be selected depending on the heating temperature, type of the plant used, the type of the cells or tissue to be heat-treated and so on, and is usually 5 seconds to 24 hours. When the heating temperature is high, the efficiency of transferring genes may be significantly promoted even if the time of the heat treatment is short. For example, when the heating temperature is 60° C., heat treatment for about 5 seconds may significantly promote the efficiency of gene transfer. On the other hand, when the heating temperature is as low as about 34° C., the efficiency of gene transfer may be promoted by heat treatment for several tens of hours. In most cases, particularly preferred heating conditions are 37° C. to 52° C. for 1 minute to 24 hours, and the appropriate heating conditions for the particular plant cells or tissue may be easily selected by a routine experiment. By heating the plant cells or plant tissue at a temperature not lower than 55° C. for a long time, the plant cells may be damaged and the efficiency of transformation may be decreased. Therefore, when the heating temperature is not lower than 55° C., the heating time is preferably short, for example, not longer than 3 minutes, preferably not longer than 1 minute so as to avoid damaging of the plant cells.

The conditions for centrifugation may appropriately be selected depending on the type of the plant used and the like, and may usually be carried out under a centrifugation acceleration of 100 G to 250,000 G, preferably 500 G to 200,000 G, more preferably 1000 G to 150,000 G. The time for centrifugation may appropriately be selected depending on the centrifugal acceleration, type of the plant used and so on, and is usually and preferably not less than one second. There is no upper limit of the centrifugation time, and about 10 minutes may usually be sufficient for attaining the object of the centrifugation. When the centrifugal acceleration is large, the efficiency of transferring genes may be significantly promoted even if the centrifugation time is very short, for example, 1 second or less. On the other hand, when the centrifugal acceleration is small, the efficiency of transferring genes may be significantly promoted by conducting the centrifugation for a long time. In most cases, especially preferred centrifugation conditions are about 500 G to 200,000 G, especially 1000 G to 150,000 G for about 1 second to 2 hours, and the appropriate centrifugation conditions for the particular plant cells or tissue may be easily selected by a routine experiment.

The method of the present invention is characterized by using the plant cells or plant tissue which were(was) heated and centrifuged, or by contacting the plant cells or plant tissue with a bacterium belonging to the genus *Agrobacterium* while conducting the heat treatment and/or centrifugation, and as the method for gene transfer or transformation per se using the bacterium belonging to the genus *Agrobacterium*, a well-known method may be applied as it is.

The method for gene transfer or transformation per se into plants using a bacterium belonging to the genus *Agrobacterium* is well-known in the art and is widely used.

It is known for a long time that a soil bacterium *Agrobacterium* (*Agrobacterium tumefaciens*) causes crown gall disease in a number of dicotyledons. In 1970s, it was discovered that Ti plasmid concerns the virulence, and that the T-DNA which is a part of Ti plasmid is incorporated into the plant genome. Thereafter, it was proved that the T-DNA contains genes participating in synthesis of hormones (cytokinins and auxins) required for induction of tumor, and that the genes are expressed in plants in spite of the fact that the genes are bacterial genes. A group of genes existing in the virulence region (vir region) in the Ti plasmid is required for the excision of T-DNA and its transfer to plants, and the border sequences existing at the both ends of the T-DNA are necessary for the T-DNA to be excised. *Agrobacterium rhizogenes* which is another bacterium belonging to the genus *Agrobacterium* has a similar system on the Ri plasmid (FIGS. 3 and 4).

Since T-DNA is incorporated into the plant genome by infection of *Agrobacterium*, it was expected that a desired gene may be incorporated into the plant genome by inserting the desired gene in the T-DNA. However, since Ti plasmid is as large as not less than 190 kb, it was difficult to insert a gene into the T-DNA by a standard technique of genetic engineering. Thus, a method for transferring a foreign gene into the T-DNA was developed.

Figure 3:
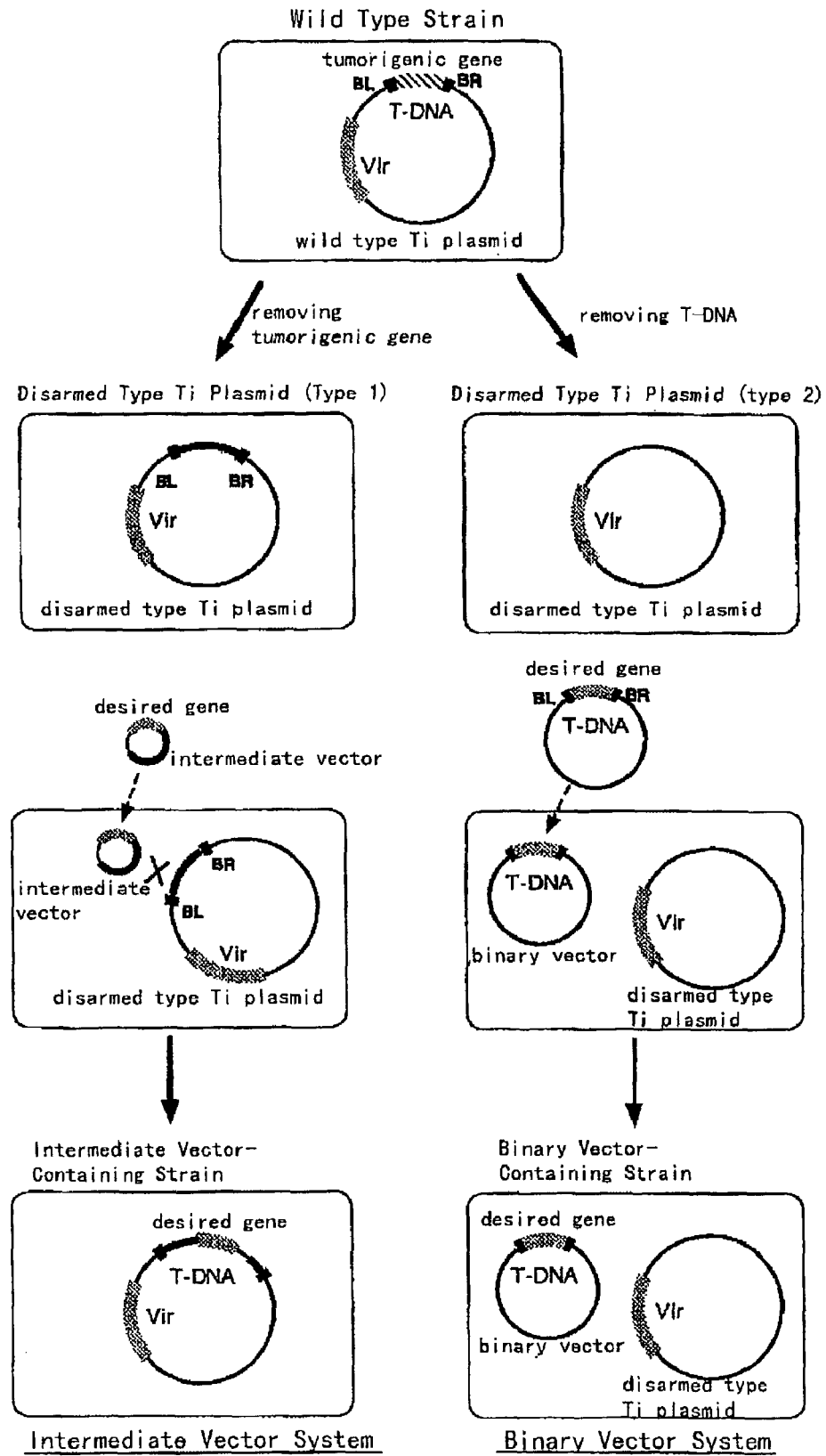
FIG. 3 is a schematic view for showing the intermediate vector system and binary vector system which are major two vector systems of bacteria belonging to genus *Agrobacterium*.
Figure 4:
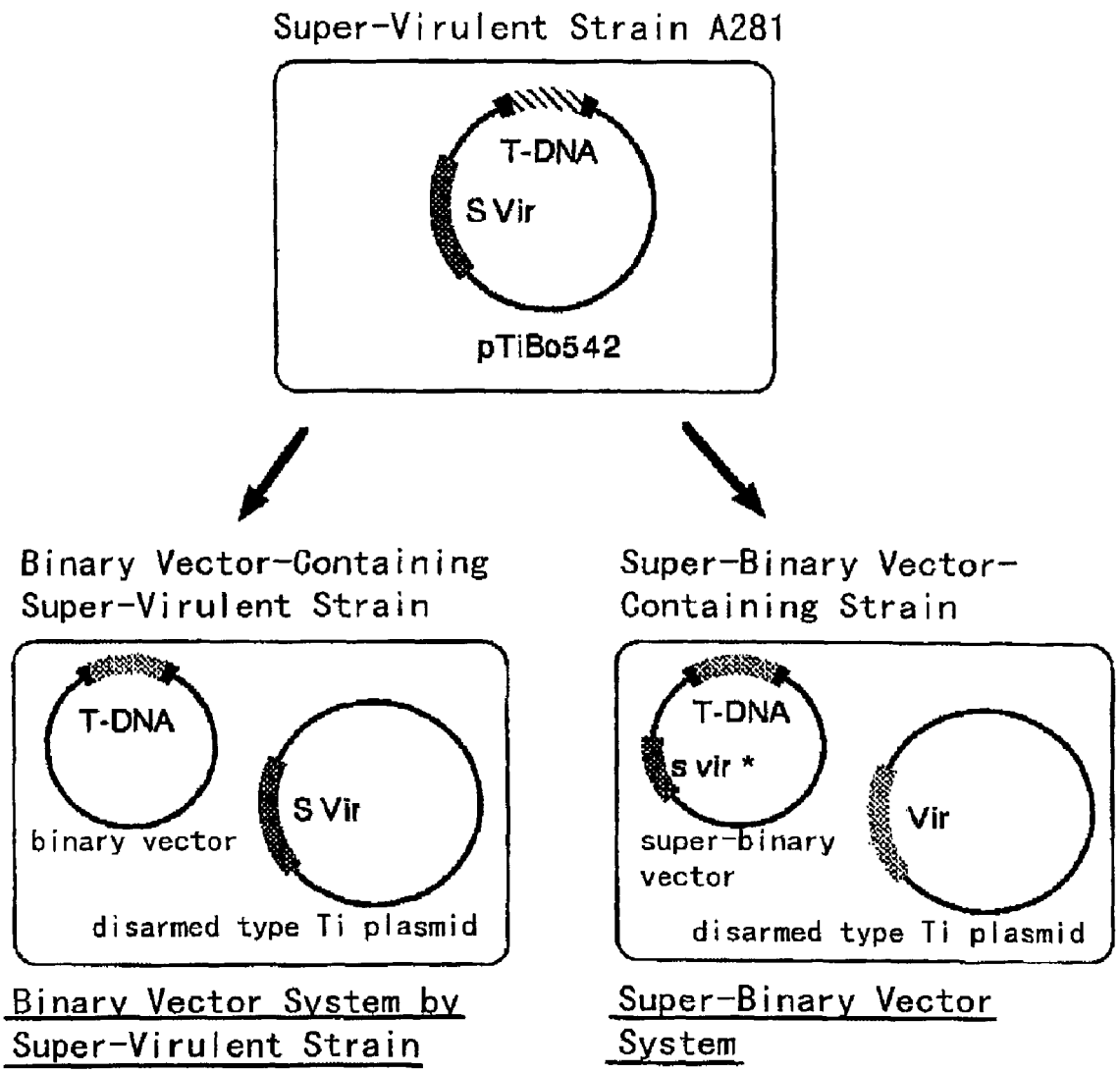
FIG. 4 is a schematic view showing two binary vector systems derived from super virulent strain A281 of *Agrobacterium tumefaciens*.

First, disarmed strains such as LBA4404 (Hoekema et al., 1983 (Reference (14))), C58C1(pGV3850) (Zambryski et al., 1983 (Reference (44))), and GV3Ti11SE (Fraley et al., 1985 (Reference (10))), that have tumorigenic Ti plasmids from which hormone synthetase genes were eliminated, were prepared (FIG. 3). Two methods employing such a strain, that is, a method by which a desired gene is transferred into the Ti plasmid of *Agrobacterium*, and a method by which a T-DNA having a desired gene is transferred into *Agrobacterium*, were developed. One of these methods is the so called intermediate vector method (Fraley et al., 1985 (Reference (10)); Fraley et al., 1983 (Reference (11)); Zambryski et al., 1983 (Reference (44)), Japanese Laid-open Patent Application (Kokai) No. 59-140885 (EP116718)). In this method, an intermediate vector which is easy to handle by genetic manipulation techniques, in which a desired gene may be inserted, and which can be replicated in *E. coli* is transferred into the T-DNA in the disarmed type Ti plasmid of *Agrobacterium* by triparental mating (Dina et al., 1980 (Reference (9))). Another method is the so called binary vector method (FIG. 3), which is based on the fact that although the vir region is necessary for the T-DNA to be incorporated into plants, it is not necessary that the T-DNA and the vir region exist in the same plasmid ((Hoekema et al., 1983 Reference (14)). The vir region contains virA, virB, virC, virD, virE and virG (Plant Biotechnology Encyclopedia (Enterprise Co., Ltd. (1989)), and the vir region is defined as those containing all of virA, virB, virC, virD, virE and virG. Thus, the binary vector is a small plasmid which is replicable in both *Agrobacterium* and *E. coli*, and this plasmid is transferred into *Agrobacterium* having a disarmed type Ti plasmid. The transferred of the binary vector into *Agrobacterium* may be carried out by electroporation method, triparental mating or the like). Binary vector includes pBIN19 (Bevan, 1984 (Reference (5))), pBI121 (Jefferson, 1987 (Reference (21))), pGA482 (An et al., 1988 (Reference (2)), Japanese Laid-open Patent Application (Kokai) No. 60-70089 (EP120516)), and a number of new binary vectors have been constructed based on these vectors. In the system of Ri plasmid, similar vectors have been constructed and are used for transformation.

*Agrobacterium* A281 (Watson et al., 1975 (Reference (42))) is a super-virulent strain, whose host spectrum is wide and whose efficiency of transformation is higher than other strains (Hood et al., 1987(Reference (15)); Komari, 1989 (Reference (23))). This feature is brought about by a Ti plasmid pTiBo542 contained in A281 (Hood et al., 1984 (Reference (18)); Jin et al., 1987 (Reference (22)); Komari et al., 1986 (Reference (26))).

Two new systems using pTiBo542 has been developed. One system utilizes strains EHA101 (Hood et al., 1986, Reference (17)) and EHA105 (Hood et al., 1993, Reference (16)) containing a Ti plasmid which is a disarmed type of pTiBo542. By applying these strains to the above-mentioned binary vector system, a system having a high efficiency of transformation was achieved, which is widely used for transformation of various plants. Another system is "super-binary" vector system (Hiei et al., 1994 (Reference (13)); Ishida et al., 1996 (Reference (20)); Komari et al., 1999 (Reference (28)), WO94/00977, WO95/06722) (FIG. 4). Since this system comprises a disarmed type Ti plasmid having the vir region (virA, virB, virC, virD, virE and virG) (each of these may also be hereinafter referred to as "vir fragment region") and a plasmid having T-DNA, this is a kind of the binary vector system. However, it is different from the binary vector in that a super-binary vector (Komari, 1990a (Reference (24))) in which a vir region fragment (preferably a fragment containing at least virB or virG, more preferably a fragment at least containing virB and virG) substantially lacking at least one of the fragments of vir region is incorporated into the plasmid having the T-DNA, i.e., the binary vector. To transfer a T-DNA region into which a desired gene has been inserted into an *Agrobacterium* having the super-binary vector, homologous recombination via the triparental mating method may be employed as an easy method (Komari et al., 1996 (Reference (27))). It has been proved that the super-binary vector gives much higher transformation efficiency than the above-described various vector systems for a number of plant species (Hiei et al., 1994 (Reference (13)); Ishida et al., 1996 (Reference (20)); Komari, 1990b (Reference (25)); Li et al., 1996 (Reference (29)); Saito et al., 1992 (Reference (38))).

In the method of the present invention, the host bacterium belonging to the genus *Agrobacterium* is not restricted, and *Agrobacterium tumefaciens* (e.g., the above-described *Agrobacterium tumefaciens* LBA4404 (Hoekema et al., 1983 (Reference (14))) and EHA101 (Hood et al., 1986 (Reference (17))) may preferably be employed.

The method of the present invention may be applied to any of the gene transfer systems as long as it is based on the expression of the group of genes in the vir region in the bacterium belonging to the genus *Agrobacterium* so as to obtain significant effect. Thus, the method of the present invention may be applied to any of the vector systems such as the above-described intermediate vectors, binary vectors, super-virulent binary vectors and super-binary vectors so as to obtain the advantageous effect of the present invention. The method of the present invention may also be applied to the vector systems obtained by modification of these vectors (e.g., those wherein the entire or a part of the vir region of a bacterium belonging to the genus *Agrobacterium* is excised and additionally incorporated into the plasmid, or the entire or a part of the vir region of a bacterium belonging to the genus *Agrobacterium* is excised and is transferred into *Agrobacterium* as a part of a new plasmid). Further, needless to say, by the method of the present invention, the efficiency of transfer of the T-DNA region of wild type *Agrobacterium* is promoted so as to promote the infection efficiency.

The desired gene to be transferred into the plant may be inserted into a restriction site in the T-DNA region of the above-described plasmid by a conventional method, and the *Agrobacterium* into which the desired gene was incorporated may be selected based on an appropriate selection marker such as a drug resistant gene against a drug such as kanamycin or paromomycin. In cases where the plasmid is large and has a number of restriction sites, it is not always easy to insert the desired DNA into the T-DNA region by an ordinary subcloning method. In such a case, the desired DNA may be inserted by the triparental mating method utilizing the homologous recombination in the cell of the bacterium belonging to the genus *Agrobacterium*.

Transfer of the plasmid into a bacterium belonging to the genus *Agrobacterium* such as *Agrobacterium tumefaciens* may be carried out by a known method including the above-mentioned triparental mating method, electroporation method, electroinjection method and chemical treatments with PEG or the like.

The gene which is to be transferred into the plant is, in principle, arranged between the left and right border sequences of the T-DNA as in the conventional method. However, since the plasmid is annular, the plasmid may contain only one border sequence. Alternatively, in cases where a plurality of genes are to be arranged at different sites, the plasmid may contain three or more border sequences. Alternatively, arrangement of the desired plasmid in the Ti or Ri plasmid may be performed in the cell of the bacterium belonging to the genus *Agrobacterium*, or the desired gene may be arranged in another plasmid. Further, the desired gene may be arranged in a plurality of types of plasmids.

Transfer of a gene into the plant cells via a bacterium belonging to the genus *Agrobacterium* may be attained by simply making the plant cells or plant tissue contact the bacterium belonging to the genus *Agrobacterium*. For example, a cell suspension of the bacterium belonging to the genus *Agrobacterium* having a population density of about $10^6$ to $10^{11}$ cells/ml is prepared, and the plant cells or the plant tissue are(is) immersed in the suspension for about 3 to 10 minutes, followed by co-culturing the resultant on a solid medium for several days, thereby attaining the transfer of the gene.

The cells or the tissue to be subjected to the gene transfer are(is) not restricted at all and may be a leaf, root, stem, fruit or any other portion of the plant. Further, dedifferentiated tissue such as a callus or a non-dedifferentiated tissue such as an embryo may be employed. The type of the plant is not restricted at all, and angiosperms are preferred. As long as the plant is an angiosperm, either dicotyledon or monocotyledon is preferred.

As will be concretely shown in the following Examples, by the method of the present invention, the efficiency of gene transfer is significantly promoted when compared with the conventional *Agrobacterium* method. Further, not only the efficiency of gene transfer to the plants to which genes were able to be transferred by the conventional *Agrobacterium* method, but also gene transfer can be first attained by the method of the present invention to the plants to which genes could not be hitherto transferred by the conventional *Agrobacterium* method. Therefore, the term "promoting efficiency of gene transfer" includes the cases where the gene transfer is first attained to the plants to which genes could not hitherto be transferred by a known method (that is, such a case can be considered as a case wherein the efficiency of gene transfer which was 0% by the known method is promoted).

EXAMPLES

The present invention will now be described by way of examples thereof. It should be noted that the present invention is not restricted to the following Examples.

Example 1

(1) Sample Tissue and Sample Strain

As the sample variety, Asanohikari which is a variety of Japonica rice was employed, and immature embryo was used as the material. Sample immature embryos were collected from immature seeds at 1 to 2 weeks after flowering and prepared by the method of Hiei, Y. et al (Reference (13)). That is, glumes of immature seeds at 7 to 12 days after flowering were removed and the seeds were sterilized with 70% ethanol for 30 seconds and with 1% aqueous sodium hypochlorite solution for 10 minutes. Thereafter, immature embryos were excised and used as the samples. Calli derived from immature embryos were obtained by culturing the immature embryos on 2N6 medium (Hiei et al. 1994 (Reference (13)) (inorganic salts and vitamins of N6 (Chu C. C. 1978 (Reference (8), 1 g/l casamino acid, 2 mg/l 2,4-D) for two weeks.

Figure 2:
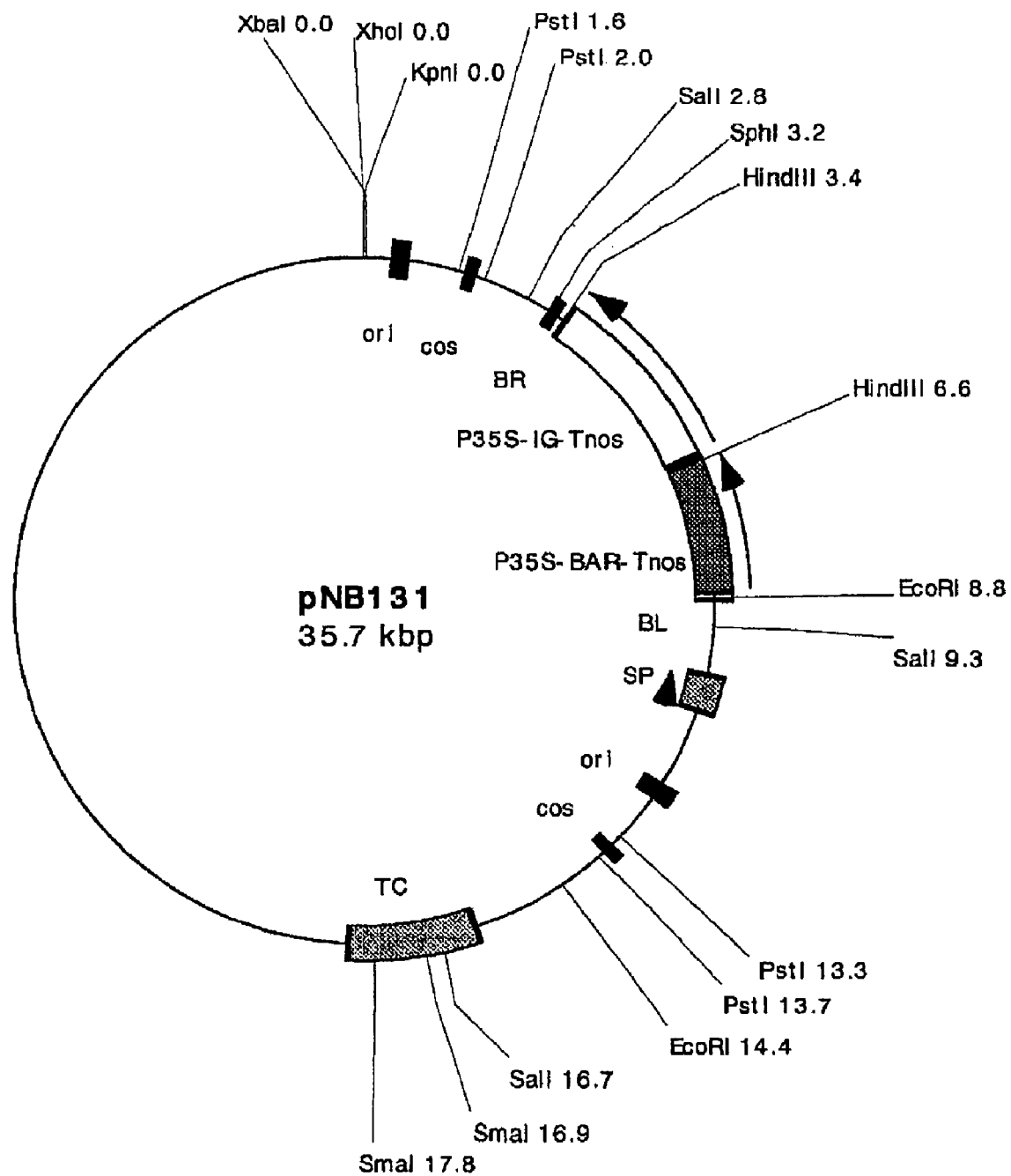
FIG. 2 is a gene map of pNB131 which is an example of super-binary vectors, that may preferably be employed in the present invention.

As the *Agrobacterium* strains and plasmid vectors, LBA4404(pIG121Hm) (Hiei et al., 1994 (Reference (13))), LBA4404(pNB131) (see FIG. 2), and LBA4404(pTOK233) (Hiei et al., 1994 (Reference (13))) were used.

Construction of pNB131 was carried out as follows: After transferring pSB31 (Ishida Y, 1996 (Reference (20))) into *E. coli* LE392, pSB31 was transferred to *Agrobacterium* LBA4404 containing pNB1(Komari T et al., 1996 (Reference (27)) by triparental mating method (Ditta G, 1980 (Reference (9)). By homologous recombination between pNB1 and pSB1 in the cell of *Agrobacterium*, pNB131 was obtained.

The T-DNA region of pIG121Hm contain a kanamycin resistant (nptII) gene driven by nos promoter, a hygromycin resistant (hpt) gene driven by 35S promoter of cauliflower mosaic virus (CaMV), and a GUS gene driven by the 35S promoter, which GUS gene contains introns of the catalase gene of castor bean (Ohta, S. et al., 1990 (Reference (33)).

The T-DNA region of pNB131 contains a bar gene driven by 35S promoter, and a GUS gene driven by the 35S promoter, which GUS gene contains introns (described above).

The T-DNA region of pTOK233 contains an nptII gene driven by nos promoter, an hpt gene driven by 35S promoter, and a GUS gene driven by the 35S promoter, which GUS gene contains introns (described above). The plasmid pTOK233 is a super-binary vector having high ability of transformation (Komari, T. et al., 1999 (Reference (28))).

(2) Heat Treatment

In a tube containing sterilized water, 5 to 200 mg of the sample tissue was immersed. Heat treatment was carried out by immersing the tube in a water bath of which temperature is set to a prescribed heat treatment temperature for several seconds to several tens hours. After the heat treatment, the tube was cooled with flowering water.

(3) Centrifugation Treatment

The sample tissue was placed in a centrifugal tube containing sterilized water, and centrifugation was performed at 25° C. at 20,000 G for 1 to 60 minutes.

(4) Infection and Co-culturing

After the heat treatment or centrifugation treatment, or combination of these treatments, the sterilized water in each tube was removed and suspension of *Agrobacterium* was added, followed by stirring the mixture with a vortex mixer for 5 to 30 seconds. Preparation of the suspension of the bacterium was carried out by Hiei Y. et al. (Reference (13)). That is, colonies of *Agrobacterium* cultured on AB medium (Chilton, M-D et al., 1974 (Reference (7))) were collected with a platinum loop and the collected bacteria were suspended in modified AA medium (AA major inorganic salts, AA amino acids and AA vitamins (Toriyama K. et al., 1985 (Reference (39)), MS minor salts (Murashige, T et al., 1962 (Reference (32)), 1.0 g/l casamino acid, 100 µM acetosyringone, 0.2 M sucrose, 0.2 M glucose). The population density of the bacterial cells in the suspension was adjusted to about 0.3 to $1 \times 10^9$ cfu/ml. After leaving the mixture of immature embryos and the suspension of *Agrobacterium* to stand at room temperature for about 5 minutes, the immature embryos were plated on a medium for co-culturing. As the medium for co-culturing 2N6-AS medium (Hiei et al. 1994 (Reference (13)) containing 8 g/l agarose as a solidifier was used. The co-culturing was carried out at 25° C. for 3 to 7 days in the dark, and a portion of the immature embryo was treated with X-Gluc to check the expression of the GUS gene (Hiei et al. 1994) (Reference (13)). That is, immediately after the co-culturing, the tissue was immersed in 0.1M phosphate buffer (pH 6.8) containing 0.1% Triton X-100, and was left to stand at 37° C. for 1 hour. After removing *Agrobacterium* with phosphate buffer, phosphate buffer containing 1.0 mM 5-bromo-4-chloro-3-indolyl-β-D-glucuronic acid (X-glue) and 20% methanol was added. After incubating the resultant at 37° C. for 24 hours, tissues colored in blue were observed under microscope.

(5) Selection of Transformed Cells (Japonica Rice)

After the co-culturing, the scutella of the grown embryos were divided into 4 to 7 pieces with a lancet and the divided scutella were cultured on 2N6 medium (described above) not containing a selection drug for several days under luminous condition. Then the scutella were transferred to 2N6 medium containing 50 to 100 mg/l hygromycin and cultured at 30° C. under luminous condition for about 2 to 3 weeks. As the medium containing 10 mg/l phosphonothricin (PPT) as a selection drug, CC medium (Potrykus et al. 1979 (Reference (34)) containing 2 mg/l 2,4-D and not containing coconut water was used. The drug resistant calli formed on the medium were transferred to N6-7 medium (Hiei et al. 1994 (Reference (13))) and secondary selection was conducted for 7 days at 30° C. under luminous condition. Each medium contained combination of 250 mg/l cefotaxime and 250 mg/l carbenicillin sodium, or contained 250 mg/l cefotaxime alone. As the medium-solidifier, 4 g/l Gelrite was used. The drug resistant calli grown on the medium was subjected to the X-Gluc treatment and expression of the GUS gene was checked as described above.

(6) Results

The results of the transient expression of the GUS gene after the heat treatment and/or the centrifugation, and after the co-culturing with LBA4404(pIG121Hm) and LBA4404 (pNB131) are shown in Tables 1 and 2. By carrying out the heat treatment or centrifugation treatment, the area in which GUS was expressed was clearly larger than the non-treated group, so that gene transfer occurred at a higher frequency. Further, by combining the heat treatment and the centrifugation treatment, the frequency was further increased.

The results of selection of the transformed calli obtained by culturing the rice immature embryos on the medium containing the selection drugs, after the co-culturing with *Agrobacterium* are shown in Tables 3, 4 and 5. The efficiency of obtaining transformed calli which were resistant to drug and which sowed uniform expression of GUS gene was prominently increased by carrying out the heat treatment or the centrifugation treatment. Further, by combining the heat treatment and the centrifugation treatment, the efficiency of transformation was higher than in the cases where only one of these treatments was performed (Tables 3, 4 and 5). Thus, it was proved that by subjecting rice embryo to combination of the heat treatment and centrifugation treatment, efficiency of transformation was further promoted when compared with the cases where only one of these treatments was performed.

Further, it was confirmed that in cases where the efficiency of gene transfer is low by the centrifugation treatment alone due to the variety or the like, the efficiency of gene transfer was prominently increased by co-employing the heat treatment. Further, it was also confirmed that by setting the temperature of the centrifuge at about 40° C. when the centrifugation is carried out, the centrifugation treatment and the heat treatment may be carried out simultaneously, and similar effect as the above-described combination of the treatments is obtained.

Hiei et al. (1994 (Reference (13))) reported that transformation may be attained with a relatively high efficiency using calli of rice. Aldemita R R et al. 1996 (Reference (1))) reported a case of transformation using rice immature embryo. To more effectively and more stably carry out these transformation methods, the above-described combined treatment method is very effective. Especially, although the quality of immature embryo is likely varied depending on the environment of culturing so that it is not easy to always obtain immature embryo suited for transformation, it may be possible to keep high efficiency of transformation by subjecting the immature embryo to the combined treatments. Hiei et al. (1994) (Reference (13)) showed that a super-binary vector having a high transformation ability promotes the efficiency of transformation of rice. According to Aldemita R R et al. 1996 (Reference (1))), transformants were obtained only in the test using LBA4404(pTOK233) containing a super-binary vector. By the combined treatment method according to the present invention, even when an ordinary binary vector is used, a high efficiency of transformation is attained, which is comparable to or even higher than that attained in the transformation using a super-binary vector. Further, by employing both the super-binary vector and the combined treatment method, the efficiency may be even more promoted. Still further, it is expected that transformants may be obtained by employing the combined treatment method for the varieties with which a transformant has not hitherto been obtained.

TABLE 1

Heat/Centrifugation Treatments and Transient Expression of GUS Gene in Scutella of Immature Embryos (Variety: Asanohikari)

| Treatment Temperature (Treatment Time) | Centrifugal Acceleration (Treatment Time) | Number of Sample Immature Embryos | Number of Immature Embryos Percentage of GUS-Expressed Area in Surface of Scutellum (%) | | | | | | |
|---|---|---|---|---|---|---|---|---|---|
| | | | 0 | 0-1 | 1-10 | 10-20 | 20-50 | 50-80 | 80-100 |
| — | — | 20 | 3 | 8 | 8 | 1 | 0 | 0 | 0 |
| 46° C. (5 min) | — | 20 | 1 | 6 | 7 | 4 | 2 | 0 | 0 |
| — | 20,000 G (30 min) | 20 | 0 | 1 | 4 | 7 | 7 | 1 | 0 |
| 46° C. (5 min) | 20,000 G (30 min) | 20 | 0 | 0 | 0 | 2 | 9 | 8 | 1 |

Sample Strain: LBA4404(pIG121Hm); Duration of Co-culturing: 5 days

TABLE 2

Heat/Centrifugation Treatments and Transient Expression of GUS Gene in Scutella of Immature Embryos (Variety: Asanohikari)

| Treatment Temperature (Treatment Time) | Centrifugal Acceleration (Treatment Time) | Number of Sample Immature Embryos | Number of Immature Embryos Percentage of GUS-Expressed Area in Surface of Scutellum (%) | | | | | | |
|---|---|---|---|---|---|---|---|---|---|
| | | | 0 | 0-1 | 1-10 | 10-20 | 20-50 | 50-80 | 80-100 |
| — | — | 20 | 3 | 13 | 4 | 0 | 0 | 0 | 0 |
| 46° C. (5 min) | — | 20 | 0 | 0 | 10 | 7 | 3 | 0 | 0 |
| — | 20,000 G (30 min) | 20 | 0 | 0 | 3 | 9 | 8 | 0 | 0 |
| 46° C. (5 min) | 20,000 G (30 min) | 20 | 0 | 0 | 0 | 3 | 14 | 3 | 0 |

Sample Strain: LBA4404(pNB131); Duration of Co-culturing: 6 days

TABLE 3

Heat/Centrifugation Treatments and Efficiency of Selection of Transformed Calli (Variety: Asanohikari)

| Treatment Temperature (Treatment Time) | Centrifugal Acceleration (Treatment Time) | Number of Sample Sections of Immature Embryo (A) | Number of Hm-resistant GUS-Positive Calli (B) | B/A (%) |
|---|---|---|---|---|
| — | — | 50 | 6 | 12.0 |
| 46° C. (5 min) | — | 51 | 15 | 29.4 |
| — | 20,000 G (30 min) | 51 | 29 | 56.9 |

TABLE 3-continued

Heat/Centrifugation Treatments and Efficiency of Selection of
Transformed Calli (Variety: Asanohikari)

| Treatment Temperature (Treatment Time) | Centrifugal Acceleration (Treatment Time) | Number of Sample Sections of Immature Embryo (A) | Number of Hm-resistant GUS-Positive Calli (B) | B/A (%) |
|---|---|---|---|---|
| 46° C. (5 min) | 20,000 G (30 min) | 46 | 29 | 63.0 |

Sample Strain: LEA4404(pIG121Hm); Duration of Co-culturing: 5 days, Hm: 100 mg/l hygromycin

TABLE 4

Heat/Centrifugation Treatments and Efficiency of Selection of
Transformed Calli (Variety: Asanohikari)

| Treatment Temperature (Treatment Time) | Centrifugal Acceleration (Treatment Time) | Number of Sample Sections of Immature Embryo (A) | Number of Hm-resistant GUS-Positive Calli (B) | B/A (%) |
|---|---|---|---|---|
| — | — | 60 | 7 | 14.7 |
| 46° C. (5 min) | — | 60 | 9 | 15.0 |
| — | 20,000 G (1 min) | 60 | 48 | 80.0 |
| — | 20,000 G (60 min) | 60 | 48 | 80.0 |
| 46° C., 5 min | 20,000 G (1 min) | 60 | 51 | 85.0 |
| 46° C., 5 min | 20,000 G (60 min) | 60 | 51 | 85.0 |

Sample Strain: LBA4404(pIG121Hm); Duration of Co-culturing: 6 days, Hm: 100 mg/l hygromycin

TABLE 5

Heat/Centrifugation Treatments and Efficiency of Selection of
Transformed Calli (Variety: Asanohikari)

| Treatment Temperature (Treatment Time) | Centrifugal Acceleration (Treatment Time) | Number of Sample Sections of Immature Embryo (A) | Number of Hm-resistant GUS-Positive Calli (B) | B/A (%) |
|---|---|---|---|---|
| — | — | 62 | 18 | 29.0 |
| 46° C. (5 min) | — | 64 | 32 | 52.5 |
| — | 20,000 G (30 min) | 60 | 39 | 65.0 |
| 46° C., 5 min | 20,000 G (30 min) | 60 | 41 | 68.3 |

Sample Strain: LBA4404(pNB131); Duration of Co-culturing: 6 days, PPT: 10 mg/l phosphinothricin Example 2

Immature embryos of maize with a size of about 1.2 mm (variety: A188, obtained from National Institute of Agrobiological Resources, The Ministry of Agriculture, Forestry and Fisheries) were aseptically collected and placed in a tube containing 2 ml of LS-inf liquid medium. After washing the embryos once with the same medium, 2.0 ml of fresh medium was added. Heat treatment was carried out by immersing the tube in a water bath at 46° C. for 3 minutes. Centrifugation treatment was performed by centrifuging the tube with a cooling centrifuge at 20 KG, at 4° C. for 30 minutes. Combined heat/centrifugation treatments were carried out by conducting the above-described heat treatment and then conducting the above-described centrifugation treatment. The control was left to stand at room temperature for the same period of time. After the treatments, the medium was removed, and 1.0 ml of a suspension of Agrobacterium tumefaciens LBA4404 (pSB131)(Ishida et al. 1986 (Reference (20)) with a population density of about $1 \times 10^9$ cfu/ml in LS-inf liquid medium containing 100 μM acetosyringone rubber was added, followed by stirring the mixture with a vortex mixer for 30 seconds. After leaving the mixture to stand at room temperature for 5 minutes, the embryos were plated on LS-AS medium containing 10 μM $AgNO_3$ such that the surface of each hypocotyl contacts the medium. After co-culturing in the dark at 25° C. for 3 days, an aliquot of the immature embryos was sampled and the transient expression of the GUS gene was checked by the treatment with X-gluc. The plasmid pSB131 is a super-binary vector.

The immature embryos after the co-culturing were cultured on a medium containing phosphinothricin (PPT) and 10 μM $AgNO_3$, thereby carrying out selection of the transformed cells. The calli grown on the selection medium were placed on a regeneration medium containing PPT, regeneration of transformed plants was carried out. A portion of a leaf of each regenerated plant was excised and the transient expression of the GUS gene was checked by the treatment with X-gluc as in Example 1. The above-described medium and method for culturing were in accordance with Ishida, Y. et al. 1996 (Reference (20)).

The results of transient expression of GUS gene when LBA4404(pSB131) was infected to the embryos after the treatments are shown in Table 6. All of the used immature embryos including the non-treated control, expression of GUS gene was observed. However, the area in which the GUS was expressed was larger in the embryos subjected to heat treatment or combination of the heat treatment and centrifugation treatment than in the control. Especially, in the group subjected to the combination of the heat treatment and centrifugation treatment, the number of the embryos which showed expression of GUS gene in large area in the surface of the scutellum of each embryo was the largest.

The results of transformation of the immature embryos infected with LBA4404(pSB131) are shown in Table 7. From the control immature embryos which were not subjected to the heat treatment, transformed plants were obtained at a efficiency of 10.7%. On the other hand, the efficiency of transformation of the immature embryos subjected to the centrifugation treatment at 20KG at 4° C. for 30 minutes was 13.3%, so that the efficiency was higher than that of the control group. The efficiency of the transformation of the embryos subjected to the heat treatment was 20%, which is about the twice that of the non-treated group. Further, the efficiency of transformation of the embryos subjected to the combined heat treatment and centrifugation treatment was 29.6% which was about three times that of the control group.

From the results described above, it was proved that the transformation efficiency is promoted by subjecting the immature embryos as the starting materials to centrifugation treatment or heat treatment before the infection, the transformation efficiency is even more promoted by combining these treatments. From these, the possibility that the maize varieties (Ishida et al. 1996 (Reference (20))) other than A188, which could not be hitherto transformed by the conventional Agrobacterium method, may be transformed by the centrifugation treatment, was suggested.

TABLE 6

Influence on Efficiency of Gene Transfer by Treatments
(Infected with LBA4404(pSB131))

| Treatment | Sample Immature Embryo | GUS +++ | ++ | + | − |
|---|---|---|---|---|---|
| Not Treated | 9 | 0 | 3 | 6 | 0 |
| Heat | 9 | 1 | 7 | 1 | 0 |
| Centrifugation | 12 | 0 | 3 | 9 | 0 |
| Heat and Centrifugation | 17 | 5 | 9 | 3 | 0 |

Transient expression of GUS gene in immature embryos after co-culturing

TABLE 7

Influence on Efficiency of Gene Transfer by Treatments
(LBA4404(pSB131) was transferred)

| Treatment | Number of Sample Immature Embryos | PPT-resistant callus (%) | PPT-resistant plant (%) | GUS + plant (%) |
|---|---|---|---|---|
| Not Treated | 28 | 9 (32.1) | 9 (32.1) | 3 (10.7) |
| Heat | 30 | 18 (60.0) | 15 (50.0) | 6 (20.0) |
| Centrifugation | 30 | 14 (46.6) | 9 (30.0) | 4 (13.3) |
| Heat and Centrifugation | 27 | 23 (85.2) | 20 (74.1) | 8 (29.6) |

Both the number of calli and number of plants do not include clones.

Example 3

Mature seeds of creeping bent grass (*Agrostis palustris* cv. Pencross, Yukijirushi Shubyo Co., Ltd.) were sterilized and placed on a medium (TG2 medium) containing MS inorganic salts, MS vitamins, 4 mg/l dicamba, 0.5 mg/l 6BA, 0.7 g/l proline, 0.5 g/l MES, 20 g/l sucrose and 3 g/l gelrite (pH 5.8), followed by culturing the seeds at 25° C. in the dark. The derived calli were subcultured on the medium having the same composition to grow embryogenic calli. The obtained embryogenic calli were transferred to liquid medium (TG2L) which had the same composition as TG2 except that it did not contain gelrite, and cultured under shaking at 25° C. in the dark to obtain cells of suspension culture. The cells of suspension culture on 3 to 4 days after the subculture were placed in a tube containing 2 ml of TG2L medium. After once washing the calli with the same medium, 2 ml of fresh medium was added. The tube was immersed in a water bath at 46° C. for 5 minutes. After removing the medium and adding the same fresh liquid medium, the resultant was centrifuged at 5000 rpm at 4° C. for 10 minutes. The control was left to stand at room temperature. The medium was removed and 1.0 ml of a suspension of *Agrobacterium tumefaciens* LBA4404 (pTOK233) (described above) in TG2-inf medium (the same composition as TG2 medium except that proline, MES and gelrite are removed and 48.46 g/l sucrose, and 36.04 g/l glucose were added) at a population density of about $1 \times 10^9$ cfu/ml was added, followed by stirring the resulting mixture for 30 seconds by a vortex mixer. After leaving the calli to stand at room temperature for 5 minutes, the calli were placed on a medium (TG2-AS medium) which was the TG2L medium supplemented with 10 g/l glucose, 100 μM acetosyringone, 4 g/l type I agarose (pH5.8), and cultured at 25° C. for 3 days i the dark. The cells were then washed three times with TG2L medium containing 250 mg/l cefotaxime and carbenicillin. The cells were then suspended in the same buffer and cultured under shaking at 25° C. in the dark at 70 rpm. One week later, the cells were subcultured on a medium having the same composition except that 50 mg/l hygromycin was added. After culturing the cells for another week, an aliquot was sampled and treated with X-gluc to check the expression of the GUS gene.

Expression of the GUS gene in the suspended cultured cells of creeping bent grass infected with LBA4404 (pTOK233) is shown in Table 8. In the control group, only one cell cluster showed expression of GUS. In contrast, in cases where the heat treatment and centrifugation treatment, about 30% of the cell clusters showed expression of GUS gene. Further, the area in which the GUS gene was expressed was larger in the cell clusters subjected to heat and centrifugation treatments than that of the control group.

The transformation of creeping bent grass was hitherto only attained by the direct transfer method, i.e., by particle gun (Zhong et al. 1993 (Reference (45)), Hartman et al. 1994 (Reference (12)), Xiao, L. et al., 1997 (Reference (43))) or by electroporation (Asano Y., 1994(Reference (3)), Asano Y. et al. 1998 (Reference (4))), and successful transformation by *Agrobacterium* method has not been reported. Assuming that the cause of the difficulty in transformation of creeping bent grass by *Agrobacterium* method is the low efficiency of the gene transfer in the known methods as can be seen from this Example, the possibility to obtain a transformed plant by the combined heat and centrifugation treatments according to the present invention was suggested.

TABLE 8

Effect of Heat and Centrifugation Treatments on Efficiency of Gene Transfer into Suspended Cultured Cells of Creeping Bent Grass

| | Number of Cell Clusters | | |
|---|---|---|---|
| Treatment | Total Number | GUS+ | GUS+ (%) |
| Heat and Centrifugation Treatment | 79 | 23 | 29.1 |
| Control | 101 | 1 | 1.0 |

Expression of GUS gene was checked two weeks after co-culturing

REFERENCES (1) Aldemita R R, Hodges T K (1996) *Agrobacterium tumefaciens*-mediated transformation of japonica and indica rice varieties. Planta 199: 612-617

(2) An, G., Evert, P. R., Mitra, A. and Ha, S. B. (1988) Binary vectors. In Gelvin, S. B. and Schilperoort, R. A. (eds.), Plant Molecular Biology Manual A3. Kluwer Academic Press, Dordrecht, pp. 1-19.

(3) Asano, Y., Ugaki, M. (1994) Transgenic plants of *Agrostis alba* obtained by electroporation-mediated direct gene transfer into protoplasts. Plant Cell Reports 13:243-246.

(4) Asano, Y., Ito, Y., Fukami, M., Sugiura, K., Fujiie, A. (1998) Herbicide-resistant transgenic creeping bentgrass plants obtained by electroporation using an altered buffer. Plant Cell Reports 17:963-967.

(5) Bevan, M. (1984) Binary *Agrobacterium* vectors for plant transformation. Nucleic Acids Res., 12, 8711-8721.

(6) Bidney, D., Scelonge, C., Martich, J., Burrus, M., Sims, L., and Huffmanm G. (1992) Microprojectile bombardment of plant tissues increases transformation frequency by *Agrobacterium tumefaciens*. Plant Mol. Biol., 18, 301-313.

(7) Chilton, M-D., Currier, T C. Farrand, S K. Bendich, A J. Gordon, M P. & Nester E W. (1974) *Agrobacterium tume-* faciens DNA and PS8 bacteriophage DNA not detected in crown gall turners. Proc. Natl. Acad. Sci. USA, 71:3672-3676
(8) Chu, C. C., (1978) Proc. Symp. Plant Tissue Culture, Science Press Peking, pp. 43-50
(9) Ditta, G., Stanfield, S., Corbin, D. and Helinski, D. R. (1980) Broad host range DNA cloning system for Gram-negative bacteria: Construction of gene bank of *Rhizobium meliloti*. Proc. Natl. Acad. Sci. USA, 77, 7347-7351.
(10) Fraley, R. T., Rogers, S. G., Horsch, R. B., Eicholtz, D. A. and Flick, J. S. (1985) The SEV system: a new disarmed Ti plasmid vector for plant transformation. Bio/technology, 3, 629-635.
(11) Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc Natl Acad Sci USA, 80, 4803-4807.
(12) Hartman, C. L., Lee, L., Day, P. R., Turner, N. E. (1994) Herbicide resistant turfgrass (*Agrostis palustris* Huds.) by biolistic transformation. Biotechnology 12:919-923.
(13) Hiei, Y., Ohta, S., Komari, T. and Kumashiro, T. (1994) Efficient transformation of rice (*Oryza sativa* L.) mediated by *Agrobacterium* and sequence analysis of the boundaries of the T-DNA. The Plant Journal, 6, 271-282.
(14) Hoekema, A., Hirsch, P. R., Hooykaas, P. J. J. and Schilperoort, R. A. (1983) A binary plant vector strategy based on separation of vir- and T-region of the *Agrobacterium tumefaciens* Ti-plasmid. Nature, 303, 179-180.
(15) Hood, E. E., Fraley, R. T. and Chilton, M.-D. (1987) Virulence of *Agrobacterium tumefaciens* strain A281 on legumes. Plant Physiol, 83, 529-534.
(16) Hood, E. E., Gelvin, S. B., Melchers, L. S. and Hoekema, A. (1993) New *Agrobacterium* helper plasmids for gene transfer to plants. Transgenic Res., 2, 208-218.
(17) Hood, E. E., Helmer, G. L., Fraley, R. T. and Chilton, M.-D. (1986) The hypervirulence of *Agrobacterium tumefaciens* A281 is encoded in a region of pTiBo542 outside of T-DNA. J. Bacteriol., 168, 1291-1301.
(18) Hood, E. E., Jen, G., Kayes, L., Kramer, J., Fraley, R. T. and Chilton, M.-D. (1984) Restriction endonuclease map of pTiBo542, a potential Ti-plasmid vector for genetic engineering of plants. Bio/technology, 2, 702-709.
(19) Horsch, R. B., Fry, J. E., Hoffmann, N. L., Eichholtz, D., Rpgers, S. G. and Fraley, R. T. (1985) A simple and general method for transferring genes into plants. Science 227, 1229-1231.
(20) Ishida, Y., Saito, H., Ohta, S., Hiei, Y., Komari, T. and Kumashiro, T. (1996) High efficiency transformation of maize (*Zea mays* L.) mediated by *Agrobacterium tumefaciens*. Nature Biotechnol, 14, 745-750.
(21) Jefferson, R. A. (1987) Assaying chimeric genes in plants: the GUS gene fusion system. Plant Mol. Biol. Rep., 5, 387-405.
(22) Jin, S., Komari, T., Gordon, M. P. and Nester, E. W. (1987) Genes responsible for the supervirulence phenotype of *Agrobacterium tumefaciens* A281. J. Bacteriol., 169, 4417-4425.
(23) Komari, T. (1989) Transformation of callus cultures of nine plant species mediated by *Agrobacterium*. Plant Sci., 60, 223-229.
(24) Komari, T. (1990a) Genetic characterization of double-flowered tobacco plant obtained in a transformation experiment. Theor. Appl. Genet., 80, 167-171.
(25) Komari, T. (1990b) Transformation of cultured cells of *Chenopodium quinoa* by binary vectors that carry a fragment of DNA from the virulence region of pTiBo542. Plant Cell Reports, 9, 303-306.
(26) Komari, T., Halperin, W. and Nester, E. W. (1986) Physical and functional map of supervirulent *Agrobacterium tumefaciens* tumor-inducing plasmid pTiBo542. J. Bacteriol., 166, 88-94.
(27) Komari, T., Hiei, Y., Saito, Y., Murai, N. and Kumashiro, T. (1996) Vectors carrying two separate T-DNAs for co-transformation of higher plants mediated by *Agrobacterium tumefaciens* and segregation of transformants free from selection markers. Plant J, 10, 165-174.
(28) Komari, T. and Kubo, T. (1999) Methods of Genetic Transformation: *Agrobacterium tumefaciens*. In Vasil, I. K. (ed.) Molecular improvement of cereal crops. Kluwer Academic Publishers, Dordrecht, pp. 43-82.
(29) Li, H.-Q., Sautter, C., Potrykus, I. and Puonti-Kaerlas, J. (1996) Genetic transformation of cassaya (*Manihot esculenta* Crantz). Nature Biotechnol., 14, 736-740.
(30) Lindsey, K., Gallois, P. and Eddy, C. (1991) Regeneration and transformation of sugarbeet by *Agrobacterium tumefaciens*. Plant Tissue Culture Manual B7:1-13. Kluwer Academic Publishers.
(31) McCormick, S. (1991) Transformation of tomato with *Agrobacterium tumefaciens*. Plant Tissue Culture Manual B6:1-9. Kluwer Academic Publishers.
(32) Murashige, T. and Skoog, F. (1962) Physiol. Plant 15:473-497.
(33) Ohta, S., Mita, S., Hattori, T., Namamura, K. (1990) Construction and expression in tobacco of a β-glucuronidase (GUS) reporter gene containing an intron within the coding sequence. Plant Cell Physiol. 31: 805-813.
(34) Potrykus I., Harms, C. T. and Lorz, H. (1979) Callus formation from cell culture protoplasts of corn (*Zea mays* L.). Theor. Appl. Genet. 54:209-214.
(36) Potrykus, I., Bilang, R., Futterer, J., Sautter, C. and Schrott, M. (1998) Agricultural Biotecnology, NY: Mercel Dekker Inc. pp. 119-159.
(37) Rogers, S. G., Horsch, R. B. and Fraley, R. T. (1988) Gene transfer in plants: Production of transformed plants using Ti plasmid vectors. Method for Plant Molecular Biology, CA: Academic Press Inc. pp. 423-436.
(38) Saito, Y., Komari, T., Masuta, C., Hayashi, Y., Kumashiro, T. and Takanami, Y. (1992) Cucumber mosaic virus-tolerant transgenic tomato plants expressing a satellite RNA. Theor. Appl. Genet., 83, 679-683.
(39) Toriyama, K. and Hinata, K. (1985) Plant Sci. 41:179-183
(40) Trick, H. N. and Finer, J. J. (1997) SAAT: sonication-assisted *Agrobacterium*-mediated transformation. Transgenic Research 6:329-336.
(41) Visser, R. G. F. (1991) Regeneration and transformation of potato by *Agrobacterium tumefaciens*. Plant Tissue Culture Manual B5:1-9. Kluwer Academic Publishers.
(42) Watson, B., Currier, T. C., Gordon, M. P., Chilton, M.-D. and Nester, E. W. (1975) Plasmid required for virulence of *Agrobacterium tumefaciens*. J Bacteriol, 123, 255-264.
(43) Xiao, L., Ha, S.-B. (1997) Efficient selection and regeneration of creeping bentgrass transformants following particle bombardment. Plant Cell reports 16:874-878.
(44) Zambryski, P., Joos, H., Genetello, C., Leemans, J., Van Montagu, M. and Schell, J. (1983) Ti plasmid vector for the introduction of DNA into plant cells without alteration of their normal regeneration capacity. EMBO J, 2, 2143-2150.

(45) Thong, H., Bolyard, M. G., Srinivasan, C., Sticklen, M. B. (1993) Transgenic plants of turfgrass (*Agrostis palustris* Huds.) from microprojectile bombardment of embryogenic callus. Plant Cell Reports 13:1-6.

The invention claimed is:

1. A method for promoting efficiency of transformation of plant embryos, plant calli or cultured plant cells by *Agrobacterium*, which comprises:
    a) heating and centrifuging said plant embryos, plant calli or cultured plant cells; and
    b) contacting said plant cells or plant tissue with the bacterium so that a gene is transferred into the plant embryos, calli, or cells;
    wherein contact between the plant cells or plant tissue and the bacterium occurs after heating and centrifuging the plant cells or plant tissue,
    wherein heating is performed at a temperature of 37° C. to 52° C. for 1 minute to 24 hours,
    wherein said centrifuging is carried out under a centrifugal acceleration of 1000 G to 150,000 G for 1 second to 4 hours and
    wherein the efficiency of transformation is increased at least twice in comparison to the efficiency of transformation by *Agrobacterium* wherein the plant cells or plant tissues are not heated or centrifuged according to steps a) and b).

2. A method for preparing a plant from plant embryos, plant calli or cultured cells comprising the method according to claim 1 and further comprising regenerating a plant from the transformed cells or tissues.

3. The method according to claim 1, wherein said plant cells or plant tissue are(is) from an angiosperm.

4. The method according to claim 2; wherein said plant is an angiosperm.

5. The method according to claim 3, wherein said plant cells or plant tissue are(is) from a monocotyledon.

6. The method according to claim 2; wherein said plant is a monocotyledon.

7. The method according to claim 5, wherein said plant cells or plant tissue are(is) from a plant belonging to family Gramineae.

8. The method according to claim 2; wherein said plant belongs to family Gramineae.

9. The method according to claim 7, wherein said plant cells or plant tissue are(is) from rice or maize.

10. The method according to claim 2; wherein said plant is rice or maize.

\* \* \* \* \*